United States Patent [19]

Karol

[11] Patent Number: 5,055,584

[45] Date of Patent: Oct. 8, 1991

[54] MALEIC DERIVATIVES OF 2,5-DIMERCAPTO-1,3,4-THIADIAZOLES AND LUBRICATING COMPOSITIONS CONTAINING SAME

[76] Inventor: Thomas J. Karol, 33 Harbor View Ave., Norwalk, Conn. 06854

[21] Appl. No.: 45,652

[22] Filed: May 4, 1987

[51] Int. Cl.$^5$ ............... C07D 285/125; C10M 135/36
[52] U.S. Cl. .................................. 548/142; 252/47.5
[58] Field of Search ....................... 548/142; 252/47.5

[56] References Cited

U.S. PATENT DOCUMENTS 4,584,114  4/1986  Gemmill ........................... 252/47.5

FOREIGN PATENT DOCUMENTS 218816  4/1987  European Pat. Off. ........... 548/142

Primary Examiner—Robert Gerstl

[57] ABSTRACT

Disclosed are reaction products of a maleic compound and 2,5-dimercapto-1,3,4-thiadiazole. The reaction products are useful as antiwear agents and antioxidants in lubricating compositions.

4 Claims, No Drawings

MALEIC DERIVATIVES OF 2,5-DIMERCAPTO-1,3,4-THIADIAZOLES AND LUBRICATING COMPOSITIONS CONTAINING SAME

BACKGROUND OF THE INVENTION

The present invention concerns novel derivatives of thiadiazole compounds. More particularly, the new thiadiazoles are derived from 2,5-dimercapto-1,3,4-thiadiazole and maleic compounds. The invention further concerns improved lubricating compositions containing said reaction products.

Additives known as antiwear agents are employed to increase the load-carrying capacity of lubricants. The antiwear agents promote the formulation of a surface film and thereby prevent wear of the contacting surfaces.

During the course of use, lubricants are susceptible to deterioration due to oxidation. The oxidative process leads to the loss of lubricating properties and inadequate protection of the device to be lubricated. Antioxidants are added to inhibit the oxidative process. Thus, it is desirable that antiwear agents possess antioxidant properties.

The most commonly used additives to exhibit antiwear and antioxidant properties are zinc dihydrocarbylphosphorodithioates. However, due to stricter environmental controls, it is particularly desirable to reduce the phosphorus content in lubricants. There is a need to develop improved lubricating compositions that are environmentally sound.

It has been surprisingly discovered that the foregoing disadvantages of the prior art lubricants can be eliminated by replacing all or part of the phosphorus-containing additive with certain maleic derivatives of 2,5-dimercapto-1,3,4-thiadiazoles.

Known reaction products of a dispersant, 2,5-dimercapto-1,3,4-thiadiazole and maleic acid have been disclosed as extreme pressure agents and corrosion inhibitors in U.S. Pat. No. 4,140,643 to Davis.

SUMMARY OF THE INVENTION

In accordance with the invention, there are provided novel reaction products of a maleic compound and 2,5-dimercapto-1,3,4-thiadiazole selected from the group of compounds having the structural formulae

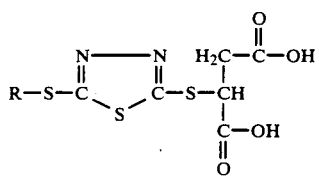

wherein R represents alkyl, hydroxyalkyl, cycloalkyl, alkyl-substituted cycloalkyl, aryl, alkylthio groups and terpene residues;

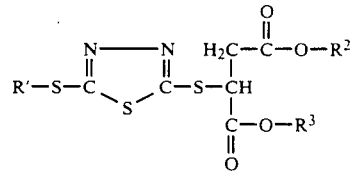

wherein R' represents hydrogen, alkyl, hydroxyalkyl, cycloalkyl, alkyl-substituted cycloalkyl, aryl, alkylthio groups and terpene residues, $R^2$ and $R^3$ represent alkyl and cycloalkyl groups and either $R^2$ or $R^3$ may be hydrogen;

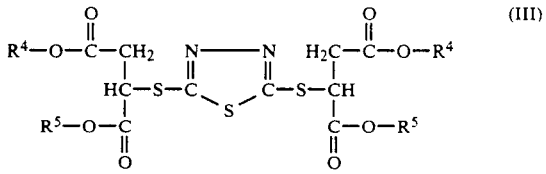

$R^4$ and $R^5$ represent alkyl and cycloalkyl groups and either $R^4$ or $R^5$ may be hydrogen; neutralization salts of said compounds and mixtures thereof.

Another aspect of the invention concerns oil-based and water-based lubricating compositions comprising a major amount of base oil or water and (a) an amount sufficient to impart antiwear and antioxidant properties of reaction products of a maleic compound and 2,5-dimercapto-1,3,4-thiadiazole selected from the group of compounds having the structual formulae I, II, and III and neutralization salts of said compounds and (b) 0 to about 1.0 percent by weight of zinc dihydrocarbylphosphorodithioate.

DESCRIPTION OF SPECIFIC EMBODIMENTS

The reaction products of formula I and II may be prepared by reacting one mole of 2,5-dimercapto-1,3,4-thiadiazole with one mole of maleic acid or maleic ester moiety followed by alkylation by known methods. The monoterpene derivatives may be prepared according to the method described in U.S. Pat. No. 2,764,547.

The 2-hydroxyalkyl substituted derivatives may be prepared by reacting 2,5-dimercapto-1,3,4-thiadiazole with the corresponding epoxide. The reaction may be conducted in the presence of an inert solvent such as alcohols, toluene and benzene and reaction promoter, for example alkylsulfonic acids. The reaction temperature will depend upon the specific reactants and solvent media employed. Typically reaction temperature will range from about 80° C. to 140° C.

Alternately, the monohydrocarbyl substituted, 2,5-dimercapto-1,3,4-thiadiazole may be prepared and subsequently reacted with the maleic moiety.

The reaction products of formula III may be prepared by reacting 2,5-dimercapto-1,3,4-thiadiazole and two moles of maleic acid or maleic anhydride to form the alpha-substituted maleic derivative and subsequently converted to the ester or half ester by reacting with an alcohol. The half ester may form on either acid group and the product is probably a mixture of both esters. Alternately, the products of formula III may be prepared directly through either the half or full ester of maleic acid.

The reaction may be conducted in an inert organic solvent such as toluene. To accelerate the rate of reaction, the reaction may be conducted in the presence of acid or Lewis acid catalysts such as methanesulfonic acid. The reaction products containing acid groups may be further reacted with inorganic metal compounds to form neutralization salts of said products. The metal compounds useful for neutralization may be selected from, among others, carbonates and oxides of sodium, calcium, magnesium and zinc.

The alkyl groups R and R' in the formula I and II represent an alkyl group having from 1 to 50 carbon atoms and a straight or branched chain including alkyls substituted by a hydroxy group. These include, among others, methyl, ethyl, n-propyl, isopropyl, n-butyl, iso-butyl, sec-butyl, pentyl, octyl, dodecyl, octadecyl and 2-hydroxyhexadecyl groups. Furthermore, R and R' represent aryl groups such as phenyl and substituted phenyl and cyclic groups. The cycloalkyl and terpene residual groups may be derived from cyclic hydrocarbons having an alpha-olefinic unsaturation. Cyclic olefins suitable for the reactions, among others, include cylohexene, methylcyclohexene, pinene and limonene.

Groups $R^2$, $R^3$, $R^4$, and $R^5$ represent alkyl groups containing 1 to 22 carbon Groups $R^2$, $R^3$, $R^4$, and $R^5$ represent alkyl groups containing 1 to 22 carbon atoms and preferably 8 to 22 carbon atoms. The cycloalkyl groups may be selected from cyclic aliphatic groups such as cyclohexyl, cyclopentyl and cycloheptyl.

The maleic derivatives of the invention are useful as lubricating additives. The compounds possess multi-functional properties with respect to antiwear and oxidation inhibition. For some applications such as motor crankcase oil, among others, the compounds provide particularly suitable lubricity improvement in lubricating compositions when used in combination with zinc dihydrocarbylphosphorodithioate.

The zinc dihydrocarbyl phosphorodithioates may be represented by the following formula:

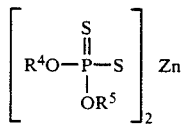

wherein $R^4$ and $R^5$ may be the same or different hydrocarbyl groups containing from 1 to 18 carbon atoms and including such groups as alkyl, alkenyl, aryl, aralkyl, alkaryl and cycloaliphatic groups. The zinc dihydrocarbyl phosphorodithioates are known compounds. They may be prepared according to known methods by esterifying phosphorodithioic acid, usually by reaction of an alcohol or phenol with $P_2 S_5$ and then neutralizing with a zinc compound such as zinc oxide.

The lubricating compositions contemplated herein include lubricating oils and lubricating greases containing a major amount of base oil. The base oil may be selected from naphthenic, aromatic, and paraffinic mineral oils. The synthetic oils may be selected from, among others, alkylene polymers, polysiloxanes, carboxylic acid esters and polyglycol ethers.

Another lubricating composition useful herein includes water-based systems. Typically the aqueous systems comprise at least 40 percent of water and zero to less than 15 percent of base oil. Oil-soluble additives are incorporated in the system with the aid of solubilizer/stabilizer systems. The water based systems are useful not only as lubricants, but also as functional fluids such as cutting oils, hydraulic fluids, and transmission fluids.

The amount of the maleic additive required to be effective for imparting antiwear and antioxidant characteristics in lubricating compositions may range from about 0.01 to 10 percent of the lubricating composition. The preferred range is 0.1 to 5 percent of the additive of the total lubricating composition.

In general, zinc dihydrocarbyl phosphorodithioates have been added to lubricating compositions up to 5% of the lubricating composition. When used with the present maleic additives, the amount may be reduced to as low as 0.1 and preferably 0.5 parts by weight per hundred parts of the lubricating base.

The lubricating compositions may contain the necessary ingredients to prepare the composition. The solid reaction products of the invention derived from lower aliphatic compounds may require a dispersing agent and emulsifier to form a uniform oil dispersion. Greases may be prepared by addition of thickeners as for example salts and complexes of fatty acids, polyurea compounds, clays and quarternary ammonium bentonite. Depending on the intended use of the lubricant, other functional additives may be added to enchance a particular property of the lubricant. The lubricating compositions may further contain known antioxidants, extreme pressure agents, metal passivators, rust inhibitors and other antiwear agents.

The following examples are given for the purpose of further illustrating the invention. All percentages and parts are based on weight unless otherwise indicated.

EXAMPLE 1

2,5-Bis(1,2-di(2-ethylhexoxycarbonyl)ethylthio)-1,3,4-thiadiazole 2,5-Dimercapto-1,3,4-thiadiazole (25.24 g, 0.17 mol), 2-ethylhexanol (91 g, 0.7 mol), and maleic anhydride (34.16 g, 0.35 mol) were charged to a reaction flask and warmed. At approximately 65° C. a solid began to form. On continued heating the reaction became fluid and was heated to 155° C. for 5 hours. Water was allowed to distill off and approximately 5 ml was collected. The reactor was fitted with a Dean Stark trap and condenser. Toluene (100 ml), and methanesulfonic acid (0.25 ml) were added by pouring slowly through the condenser. The remaining water was azeotroped off over a two hour time span. The reaction was cooled and calcium carbonate (about 2 g) was charged and stirred for ten minutes. The reaction was filtered using filter aid and stripped of solvent at reduced pressure (20mm Hg) on the rotary evaporator. This afforded 139.7 g of the product.

EXAMPLE 2

2,5-Bis(1,2-di(butoxycarbonyl)ethylthio)-1,3,4-thiadiazole 2,5-Dimercapto-1,3,4-thiadiazole (50.09 g, 0.33 mol) and dibutyl maleate (157.0 g, 0.69 mol) were charged in a reaction flask and heated to 55° C. for 4 hours. The reaction product was filtered warm using filter aid.

EXAMPLE 3

2,5-Bis(1,2-dihexoxycarbonylethylthio)-1,3,4-thiadiazole

Hexanol (72 g, 0.7 mol), and maleic anhydride (34. g, 0.35 mol) were charged into a reaction flask and heated to 120° C. for 0.5 hour. Then 2,5-dimercapto-1,3,4-thiadiazole (25 g, 0.17 mol) was charged and the reaction was heated to 155° C. for 2 hours. Hexanol (25 ml), toluene (50 ml), and 70% methanesulfonic acid (0.25 ml) were charged after fitting the reactor with a Dean Stark trap and condenser. After removal of residual water the product was cooled and calcium carbonate (about 1 g) was added and stirred 10 minutes. The product had a sweet odor.

EXAMPLE 4

2-(2-Hydroxyhexadecyl)thio-5-(1,2-di(2-ethylhexoxycarbonyl)ethylthio-1,3,4-thiadiazole 2,5-Dimercapto-1,3,4-thiadiazole (35 g, 0.23 mol), 2-ethylhexanol (61.4 g, 0.47 mol) and acetone (60 ml) were charged to a reaction vessel. 1,2-Epoxyhexadecane (55.2 g, 0.23 mol) was slowly added while maintaining the temperature at less than 30° C. After the addition, the reaction was stirred for 0.25 hours and then heated to reflux. The reaction was cooled and maleic anhydride (23 g, 0.24 mol) was charged. The reaction was then heated to reflux for 0.5 hour. At this time, solvent was distilled until the pot temperature reached 155° C. The reaction was maintained at 155° C. for 3 hours, stripped of solvent with reduced pressure (20 mm Hg at 155° C.), cooled to about 120° C. and filtered warm using filter aid.

EXAMPLE 5

2-(2-Pinanylthio)-5-(1,2-dibutoxycarbonylethylthio)-1,3,4-thiadiazole 2,5-Dimercapto-1,3,4-thiadiazole (35.0 g, 0.23 mol) was charged into a reaction flask along with alpha-pinene (33.85 g, 0.24 mol). The reaction was heated to 100° C. for 1 hour and then cautiously heated to 120° C. The reaction exothermed and was maintained at 155° C. for 20 min. Dibutyl maleate (53.5 g, 0.55 mol) was added and the reaction was maintained at 155° C. for 3 hours. The reaction product was then cooled, charged with sodium carbonate (about 1 g) and stirred. The product was filtered using a filter aid.

EXAMPLE 6

2-(2-Pinanylthio)-5-(1,2-dihexoxycarbonylethylthio)-1,3,4-thiadiazole

Hexanol (340 g, 3.33 mol). maleic anhydride (154 g, 1.67 mol) and alpha-pinene (225 g, 1.65 mol) were charged to a reaction flask. The reaction was heated to 100° C. and maintained 0.5 hours. Toluene (150 ml) and 2,5-dimercapto-1,3,4-thiadiazole (230 g, 1.53 mol) were charged. The reaction was heated to reflux at 155° C. and water was removed as it was formed. The theoretical amount of water was collected after about 4 hours. The solvent was stripped from the reaction product by rotary evaporation (20 mm Hg, 155° C.). The product was filtered warm. The product had a sweet odor.

EXAMPLE 7

Mixed half esters of 2-(2-pinanylthio)-1,3,4-thiadiazole-5-thione 2,5-Dimercapto-1,3,4-thiadiazole (35.0 g, 0.23 mol), alpha-pinene (35.0 g, 0.26 mol) and 2-ethylhexanol (31.0 g, 0.24 mol) were charged to the reaction flask. The reaction was heated to 120° C. and then slowly to 155° C. Thereafter maleic anhydride (23.0 g, 0.23 mol) was added. The reaction was maintained at 155° C. for 3 hours, stripped under reduced pressure (20 ms Hg) and filtered. The product was a mixture of 5-(1-carboxy-2-(2-ethylhexoxycarbonylethylthio)- and 5-(2-carboxy-1-(2-ethylhexoxycarbonylethylthio)-(2-pinanylthio)-1,3,4-thiadiazole half esters.

EXAMPLE 8

The additives of the invention were evaluated by the following tests.

1. Shell Four-Ball Wear Test

The test was conducted essentially according to the method described in ASTM D-2266 procedure. Four lightly polished steel balls 12.5 mm in diameter were placed in a test cup and submerged in the test sample. The test oil was Sunvis TM 21 manufactured by Sun Oil Company. The test was carried out at a rotation speed of 1800 rpm under a load of 40 kg at 54.50° C.

Although not a quantitative tool for measuring wear, the test was designed to determine qualitatively the lowest amount of additive that afforded wear protection. A rating of "failed" was assigned to scars measuring greater than 1.0 mm in diameter and "passed" to those measuring less than 1.0 mm in diameter.

2. Thin Film Oxygen Uptake Test

The test was conducted essentially according to the method described by Chia-Soon Ku et al., *J. Am. Soc. Lubricating Eng.*, 40, 2,75–83, 1984. The oxidation induction time of the lubricant was measured under conditions which simulate the high temperature oxidation process in automative engines by a modified rotary bomb oxidation test method ASTM D-2272. The test was conducted with 1.5 gram samples of SAE 30 SF/CC motor oil formulation with catalyst obtained from the National Bureau of Standards. The oil contained 0.11% phosphorus.

Additives of the invention were added to the oil in the amount indicated in Table II. The test was conducted at 160° C. and initial oxygen pressure of 620.6 kPa (90 psi). A "pass" oil has a high induction time, while a "fail" oil has a low induction time. The additives of the invention have good antioxidant properties as shown by data compiled in Table II.

TABLE I

FOUR-BALL WEAR TEST

| Sample | Active Ingredient | Percent | Scar Protection |
|---|---|---|---|
| 1 | None | — | failed |
| 2 | Zinc di(2-ethylhexyl)phosphorodithioate | 0.05 | failed |
| 3 | Zinc di(2-ethylhexyl)phosphoradithioate | 0.10 | passed |
| 4 | 2,5-Bis(1,2-di(2-ethylhexoxycarbonyl)-ethylthio)-1,3,4-thiadiazole | 0.10 | passed |
| 5 | 2,5-Bis(1.2-dibutoxycarbonyl-ethylthio)-1,3,4-thiadiazole | 0.10 | passed |
| 6 | 2,5-Bis(1,2-dihexoxycarbonyl-ethylthio)-1,3,4-thiadiazole | 0.05 | passed |
| 7 | 2-(2-Hydroxyhexadecyl)thio-5-(1,2-di(2-ethylhexoxycarbonyl)-ethylthio-1,3,4-thiadiazole | 0.10 | passed |
| 8 | 2-(2-Pinanylthio)-5-(1,2-dibutoxycarbonylethylthio)-1,3,4-thiadiazole | 0.25 | passed |
| 9 | Mixed maleic half esters of 2-(2-pinanylthio)-1,3,4-thiadiazole (Example 7) | 0.05 | passed |
| 10 | 2-(2-Pinanylthio)-5-(1,2-dihexoxycarbonylethylthio-1,3,4-thiadiazole | 0.05 | passed |

TABLE II

THIN FILM OXYGEN UPTAKE TEST

| Sample | Active Ingredient | Percent | Average Induction Time, Min. |
|---|---|---|---|
| 11 | None | — | 55.0 |
| 12 | 2,5-Bis(1,2-dihexoxycarbonylethylthio)-1,3,4-thiadiazole | 0.35 | 136.5 |
| 13 | 2-(2-Pinanylthio)-5-(1,2-dihexoxycarbonylethylthio)-1,3,4-thiadiazole | 0.35 | 159.0 |

The above embodiments have shown various aspects of the present invention. Other variations will be evident to those skilled in the art and such modifications are intended to be within the scope of the invention as defined by the appended claims.

What is claimed is:

1. A reaction product of a maleic compound and 2,5-dimercapto-1,3,4-thiadiazole selected from the group of compounds having the structural formulae

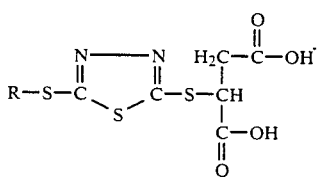

wherein R represents alkyl, hydroxyalkyl, cycloalkyl, alkyl-substituted cycloalkyl, aryl, alkylthio groups and terpene residues; and

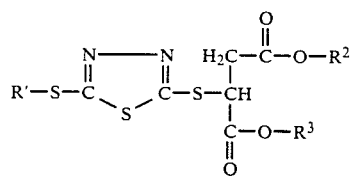

wherein R' represents alkyl, hydroxyalkyl, cycloalkyl, alkyl-substituted cycloalkyl, aryl, alkylthio groups and terpene residues, $R^2$ and $R^3$ represent alkyl and cycloalkyl groups and either $R^2$ and $R^3$ may be hydrogen; neutralization salts of said compounds and mixtures thereof.

2. A composition comprising a major amount of oil of lubricating viscosity wherein said oil is a petroleum hydrocarbon oil or a synthetic oil and from about 0.01 to 10 percent by weight of a reaction product of a maleic compound and 2,5-dimercapto-1,3,4-thiadiazole selected from the group of compounds having the structural formulae

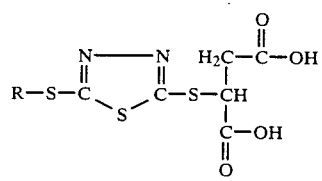

wherein R represents alkyl, hydroxyalkyl, cycloalkyl, alkyl-substituted cycloalkyl, aryl, alkylthio groups and terpene residues; and

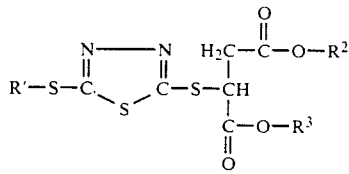

wherein R' represents alkyl, hydroxyalkyl, cycloalkyl, alkyl-substituted cycloalkyl, aryl, alkylthio groups and terpene residues, $R^2$ and $R^3$ represent alkyl and cycloalkyl groups and either $R^2$ and $R^3$ may be hydrogen; neutralization salts of said compounds and mixtures thereof.

3. A composition according to claim 2 which further contains up to 1.0 percent by weight of zinc dihydrocarbylphosphorodithioate wherein the hydrocarbyl groups are selected from the group consisting of alkyl, alkenyl, aryl, aralkyl, alkaryl and cycloaliphatic groups.

4. A composition comprising at least 40 percent by weight of water, from 0 to 15 percent by weight of a petroleum hydrocarbon oil or a synthetic oil and from about 0.01 to 10 percent by weight of a reaction product of a maleic compound and 2,5-dimercapto-1,3,4-thiadiazole selected from the group of compounds having the structural formulae

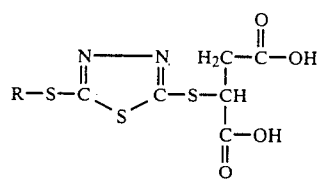

wherein R represents alkyl, hydroxyalkyl, cycloalkyl, alkyl-substituted cycloalkyl, aryl, alkylthio groups and terpene residues;

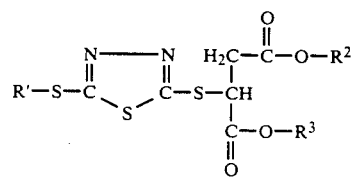

wherein R' represents hydrogen, alkyl, hydroxyalkyl, cycloalkyl, alkyl-substituted cycloalkyl, aryl, alkylthio groups and terpene residues, $R^2$ and $R^3$ represent alkyl and cycloalkyl groups and either $R^2$ and $R^3$ may be hydrogen;

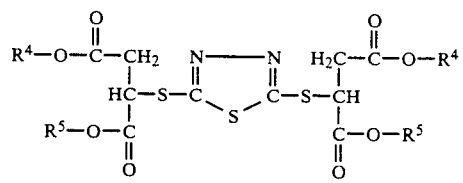

wherein $R^4$ and $R^5$ represent alkyl and cycloalkyl groups and either $R^4$ or $R^5$ may be hydrogen and wherein said alkyl groups have from 1 to 50 carbon atoms and the terpene residues are derived from pinene or limonene; neutralization salts of said compounds and mixtures thereof.

* * * * *

UNITED STATES PATENT AND TRADEMARK OFFICE
CERTIFICATE OF CORRECTION

PATENT NO. : 5,055,584

DATED : Oct. 8, 1991

INVENTOR(S) : Thomas J. Karol

It is certified that error appears in the above-identified patent and that said Letters Patent is hereby corrected as shown below:

Column 4, line 61
"55°C" should be -- 155°C -- ;

Column 5, line 68
"20 ms" should be -- 20 mm -- .

Signed and Sealed this

Twelfth Day of January, 1993

Attest:

DOUGLAS B. COMER

Attesting Officer

Acting Commissioner of Patents and Trademarks